United States Patent [19]

Förster et al.

[11] Patent Number: 5,169,427

[45] Date of Patent: Dec. 8, 1992

[54] HERBICIDAL CYCLOALKYL-SUBSTITUTED THIADIAZOLYLOXYACETAMIDES

[75] Inventors: Heinz Förster; Hans-Joachim Diehr, both of Wuppertal; Bernd Baasner; Ernst Kysela, both of Bergisch Gladbach; Albrecht Marhold, Leverkusen; Karl-Rudolf Gassen, Odenthal; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 706,127

[22] Filed: May 28, 1991

[30] Foreign Application Priority Data

Jun. 8, 1990 [DE] Fed. Rep. of Germany ....... 4018352

[51] Int. Cl.$^5$ .................... C07D 285/13; A01N 43/82
[52] U.S. Cl. .......................... 71/90; 540/603; 546/165; 546/209; 548/136
[58] Field of Search ............. 548/136; 71/90; 540/603; 546/165, 709

[56] References Cited

U.S. PATENT DOCUMENTS 4,756,741 7/1988 Forster ..................................... 71/90

FOREIGN PATENT DOCUMENTS 0348736 1/1990 European Pat. Off. .
0410551 1/1991 European Pat. Off. .
3722320 1/1989 Fed. Rep. of Germany .

Primary Examiner—Robert Gerstl
Attorney, Agent, or Firm—Sprung Horn Kramer & Woods

[57] ABSTRACT

Herbicidal cycloalkyl-substituted thiadiazolyloxyacetamides of the formula $$R^3 \underset{S}{\overset{N-N}{\diagdown}} O-CH_2-CO-N \diagdown \underset{R^2}{\overset{R^1}{\diagup}} \quad (I)$$

in which
R$^1$ represents hydrogen, or represents an optionally substituted radical selected from the group consisting of alkyl, alkenyl, alkynyl and aralkyl,
R$^2$ represents an optionally substituted radical selected from the group consisting of alkyl, alkenyl, alkynyl, cycloalkyl, cycloalkenyl, aralkyl, aryl, alkoxy, alkenyloxy and alkynyloxy, or
R$^1$ and R$^2$, together with the nitrogen atom to which they are bonded, form an optionally substituted saturated or unsaturated nitrogen-heterocyclic radical, which can contain further hetero atoms and to which a benzo grouping can be fused, and
R$^3$ represents optionally substituted cycloalkyl.

Intermediates of the formula $$R^3 \underset{S}{\overset{N-N}{\diagdown}} S-CH_3 \quad \text{and} \quad R^3 \underset{S}{\overset{N-N}{\diagdown}} SO_2-CH_3$$

are also new.

7 Claims, No Drawings

HERBICIDAL CYCLOALKYL-SUBSTITUTED THIADIAZOLYLOXYACETAMIDES

The invention relates to new cycloalkyl-substituted thiadiazolyloxyacetamides, a process and new intermediates for their preparation and their use as herbicides.

It is already known that certain phenyl-substituted thiadiazolyloxyacetamides have herbicidal properties (compare DE-OS (German Published Specification) 3,038,635, European Patent A-29,171 and European Patent A-60,426). However, the herbicidal activity of these compounds is not always completely satisfactory.

New cycloalkyl-substituted thiadiazolyloxyacetamides of the general formula (I)

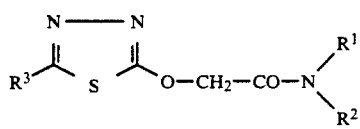

in which

R$^1$ represents hydrogen, or represents an optionally substituted radical from the series comprising alkyl, alkenyl, alkynyl and aralkyl, R$^2$ represents an optionally substituted radical from the series comprising alkyl, alkenyl, alkynyl, cycloalkyl, cycloalkenyl, aralkyl, aryl, alkoxy, alkenyloxy and alkynyloxy, or R$^1$ and R$^2$, together with the nitrogen atom to which they are bonded, form an optionally substituted saturated or unsaturated nitrogen-heterocylic radical, which can contain further hetero atoms and to which a benzo grouping can be fused, and R$^3$ represents optionally substituted cycloalkyl, have now been found It has furthermore been found that the new cycloalkylsubstituted thiadiazolyloxyacetamides of the general formula (I) are obtained by a process in which methylsulphonylthiadiazoles of the general formula (II)

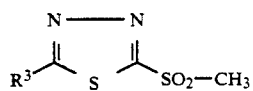

in which

R$^3$ has the abovementioned meaning, are reacted with hydroxyacetamides of the general formula (III)

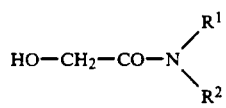

in which

R$^1$ and R$^2$ have the abovementioned meanings, if appropriate in the presence of a diluent, if appropriate in the presence of an acid-binding agent and if appropriate in the presence of a catalyst.

Finally, it has been found that the new cycloalkylsubstituted thiadiazolyoxyacetamides of the general formula (I) have interesting herbicidal properties.

The invention preferably relates to compounds of the formula (I) in which

R$^1$ represents hydrogen, or C$_1$–C$_8$-alkyl, which is optionally substituted by fluorine, chlorine, cyano or C$_1$–C$_4$-alkoxy, or represents C$_2$–C$_8$-alkenyl, which is optionally substituted by fluorine and/or chlorine, or represents C$_2$–C$_8$-alkynyl, or represents benzyl, R$^2$ represents C$_1$–C$_8$-alkyl, which is optionally substituted by fluorine, chlorine, cyano or C$_1$–C$_4$-alkoxy, or represents C$_2$–C$_8$-alkenyl, which is optionally substituted by fluorine and/or chlorine, or represents C$_2$–C$_8$-alkynyl, or represents C$_3$–C$_8$-cycloalkyl, which is optionally substituted by chlorine and/or C$_1$–C$_3$-alkyl, or represents C$_5$- or C$_6$-cycloalkenyl, or represents benzyl, which is optionally substituted by fluorine, chlorine and/or C$_1$–C$_4$-alkyl, or represents phenyl, which is optionally substituted by fluorine, chlorine, bromine, iodine, cyano, nitro, C$_1$–C$_4$-alkyl, trifluoromethyl, C$_1$–C$_4$-alkoxy and/or C$_1$–C$_4$-alkylthio, or represents C$_1$–C$_8$-alkoxy, which is optionally substituted by C$_1$–C$_4$-alkoxy, or represents C$_3$–C$_4$-alkenyl-oxy, or R$^1$ and R$_2$, together with the nitrogen atom to which they are bonded form a saturated or unsaturated five- to seven-membered nitrogen-heterocyclic radical which is optionally substituted by one to three C$_1$–C$_3$-alkyl radicals and is optionally benzo-fused, and R$_3$ represents C$_3$–C$_6$-cycloalkyl, which is optionally substituted by halogen, C$_1$–C$_4$-alkyl and/or C$_1$–C$_4$-halogenoalkyl.

The invention particularly relates to compounds of the formula (I) in which

R$^1$ represents C$_1$–C$_4$-alkyl, allyl or propargyl,

R$^2$ represents C$_1$–C$_8$-alkyl, C$_1$–C$_2$-alkoxy-C$_1$–C$_2$-alkyl, allyl, propargyl, cyclopentyl, cyclohexyl, cyclohexenyl, benzyl, phenyl (which is optionally substituted by fluorine, chlorine, bromine, cyano, nitro, methyl, ethyl, trifluoromethyl, methoxy or ethoxy), C$_1$–C$_6$-alkoxy or C$_1$–C$_2$-alkoxy-C$_1$–C$_2$-alkoxy, or R$^1$ and R$^2$, together with the nitrogen atom to which they are bonded, represent piperidinyl which is optionally substituted by one to three methyl and/or ethyl radicals, or represent pyrrolidinyl which is optionally substituted by one or two methyl and/or ethyl radicals, or represent perhydroazepinyl, or represent 1,2,3,4-tetrahydroquinolinyl, and R$^3$ represents cyclopropyl or cyclobutyl, in each case substituted by fluorine and/or chlorine and optionally additionally by methyl.

Particularly preferred compounds are those of the formula (Ia)

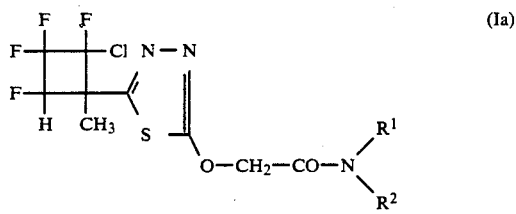

in which

R$^1$ and R$^2$ have the meanings given above as particularly preferred.

If, for example, 2-methylsulphonyl-5-(1-methyl-2-chloro 2,3,3-trifluoro-1-cyclobutyl)-1,3,4-thiadiazole and hydroxyacetic acid diethylamide are used as starting substances, the course of the reaction in the process according to the invention can be represented by the following equation:

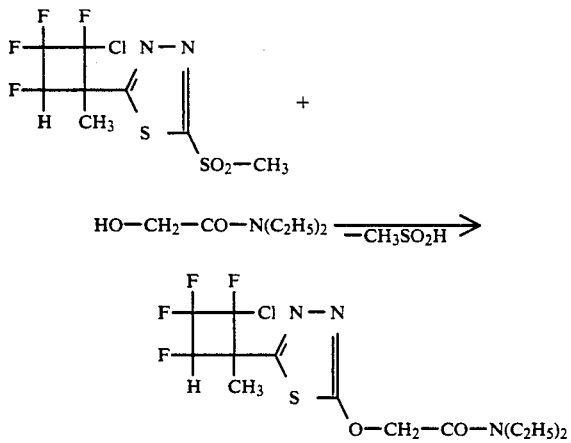

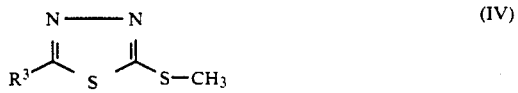

Formula (II) provides a general definition of the methylsulphonylthiadiazoles to be used as starting substances in the process according to the invention for the preparation of compounds of the formula (I).

In formula (II) $R^3$ preferably or in particular has that meaning which has already been mentioned above as being preferred or particularly preferred for $R^3$ in connection with the description of the compounds of the formula (I) according to the invention.

The starting substances of the formula (II) are not yet known from the literature, and the present invention likewise relates to these substances.

The new compounds of the formula (II) are obtained by a process in which methylthio-thiadiazoles of the general formula (IV)

in which $R^3$ has the abovementioned meaning, are reacted with an oxidizing agent, such as, for example, hydrogen peroxide, if appropriate in the presence of a catalyst, such as, for example, sodium tungstate, and if appropriate in the presence of diluents, such as, for example, water, formic acid and/or acetic acid, at temperatures between 0° C. and 100° C.

Formula (IV) provides a general definition of the methylthiothiadiazoles required as intermediates. In formula (IV), $R^3$ preferably or in particular has that meaning which has already been mentioned above as preferred or particularly preferred for $R^3$ in connection with the description of the compounds of the formula (I) according to the invention.

The intermediates of the formula (IV) are not yet known from the literature, and the present invention likewise relates to such compounds.

The new compounds of the formula (IV) are obtained by a process in which carboxylic acid chlorides of the general formula (V)

$$R^3-CO-Cl \quad (V)$$

in which $R^3$ has the abovementioned meaning, are reacted with methyl dithiocarbazate in the presence of a reaction auxiliary, such as, for example, pyridine, and if appropriate in the presence of a diluent, such as, for example, tetrahydrofuran, and the product is then reacted with sulphuric acid, in each case at temperatures of between −10° C. and +30° C. (compare the preparation examples).

The carboxylic acid chlorides of the formula (V) are known and/or can be prepared by processes which are known per se.

2-Chloro-1-methyl-2,3,3-trifluoro-cyclobutane-1-carbonyl chloride of the formula (Va)

(Va)

```
    F   F
    |   |
F———————Cl
    |   |
    |   |———CO—Cl
    |
    CH₃
``` is not yet known from the literature but is the subject of German Patent Application 3,933,750 corresponding to U.S. Ser. No. 504,463, filed April 4, 1990, now pending.

The preparation of the compound of the formula (Va) is described in the preparation examples.

Formula (III) provides a general definition of the hydroxyacetamides furthermore to be used as starting substances in the process according to the invention for the preparation of compounds of the formula (I).

In formula (III) $R^1$ and $R^2$ preferably or in particular have those meanings which have already been mentioned above as preferred or particularly preferred for $R^1$ and $R^2$ in connection with the description of the compounds of the formula (I) according to the invention.

The hydroxyacetamides of the formula (III) are known and/or can be prepared by processes which are known per se (compare U.S Pat. No. 4,509,971 and U.S. Pat. No. 4,645,525; and furthermore U.S. Pat. No. 4,334,073, DE-OS (German Published Specification) 3,038,598, DE-OS (German Published Specification) 3,038,636, European Patent A-37,526, European Patent A-348,737 and DE-OS (German Published Specification) 3,819,477).

The process according to the invention for the preparation of the new cycloalkyl-substituted thiadiazolyloxyacetamides of the formula (I) is preferably carried out using diluents. These include, preferably, hydrocarbons, such as, for example, toluene, xylene or cyclohexane, halogenohydrocarbons, such as, for example, methylene chloride, ethylene chloride, chloroform or chlorobenzene, ethers, such as, for example, diethyl ether, dipropyl ether, diisopropyl ether, dibutyl ether, diisobutyl ether, glycol dimethyl ether, tetrahydrofuran and dioxane, alcohols, such as, for example, methanol, ethanol, propanol, isopropanol or butanol, ketones, such as, for example, acetone, methyl ethyl ketone, methyl isopropyl ketone and methyl isobutyl ketone, esters, such as, for example, methyl acetate and ethyl acetate, amides, such as, for example, dimethylformamide, dimethylacetamide and N-methyl-pyrrolidone, nitriles, such as, for example, acetonitrile and propionitrile, sulphoxides, such as, for example, dimethyl sulphoxide, and water or aqueous salt solutions.

Salts which are preferably used here are the chlorides or sulphates of alkali metals or alkaline earth metals, such as, for example, sodium chloride, potassium chloride or calcium chloride. Sodium chloride is particularly preferred.

The process according to the invention is advantageously carried out using acid-binding agents. Acid-binding agents which are preferably used are strongly basic alkali metal and alkaline earth metal compounds, for example oxides, such as, for example, sodium oxide, potassium oxide, magnesium oxide and calcium oxide, hydroxides, such as, for example, sodium hydroxide, potassium hydroxide, magnesium hydroxide and calcium hydroxide, and/or carbonates, such as, for example, sodium carbonate, potassium carbonate, magnesium carbonate and calcium carbonate.

The addition of 0.01 to 10% by weight (based on the glycolic acid amide of the formula (III) employed) of a phase transfer catalyst may prove to be advantageous in some cases. Examples which may be mentioned of such catalysts are: tetrabutylammonium chloride, tetrabutylammonium bromide, tributyl-methylphosphonium bromide, trimethyl-$C_{13}/C_{15}$-alkyl-ammonium chloride, dibenzyl-dimethyl-ammonium methylsulphate, dimethyl-$C_{12}/C_{14}$-alkyl-benzylammonium chloride, tetrabutylammonium hydroxide, 18-crown-6, triethylbenzylammonium chloride, trimethylbenz-ylammonium chloride and tetraethylammonium bromide.

The reaction temperatures can be varied within a substantial range in the process according to the invention. The reaction is in general carried out at temperatures between $-50°$ C. and $+110°$ C., preferably at temperatures between $-20°$ C. and $+100°$ C.

The process according to the invention is in general carried out under normal pressure, but it can also be carried out under increased or reduced pressure, for example between 0.1 and 10 bar.

For carrying out the process according to the invention, in general 0.5 to 5 mol preferably 0.8 to 1.5 mols of hydroxyacetamide of the formula (III) are employed per mol of methylsulphonylthiadiazole of the formula (II). The reaction components can be brought together in any desired sequence. The reaction mixture is in each case stirred until the reaction has ended, and the mixture is worked up by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Apparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for combating monocotyledon weeds in dicotyledon crops, in some cases also in monocotyledon crops (such as, for example, in paddy rice). They are particularly suitable for combating harmful grasses (such as, for example, Echinochloa) in rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. A liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Possible components for the mixtures are known herbicides, such as, for example, 1-amino-6-ethylthio-3-(2,2- dimethylpropyl)-1,3,5-triazine-2,4(1H,3H)-dione [AMETHYDIONE] or N-(2-benzothiazolyl)-N,N,-dimethyl-urea (METABENZOTHIAZURON) for combating weeds in cereals; 4-amino3-methyl-6-phenyl-1,2,4-triazine-5(4H)-one (METAMITRON) for combating weeds in sugar beets, and 4-amino-6-(1,1-dimethylethyl)-3-methylthio-1,2,4-triazine-5(4-triazine-5(4H)-one (METRIBUZIN) for combating weeds in soy beans. Surprisingly, some mixtures also show a synergistic action.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect In general, the amounts used are between 60 and 4000 g of active compound per hectare of soil surface, preferably between 120 and 2000 g per ha.

The preparation and use of the active compounds according to the invention can be seen from the following examples

PREPARATION EXAMPLES

Example 1

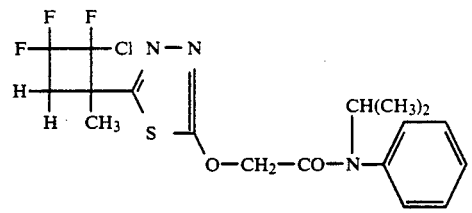

A solution of 0.92 g (23 mmol) of sodium hydroxide in 6 ml of water is added dropwise to a mixture, cooled to $-20°$ C., of 7.6 g (23 mmol) of 2-methylsulphonyl-5(1-methyl-2-chloro-2,3,3-trifluoro -1-cyclobutyl)-1,3,4thiadiazole, 4.4 g (23mmol) of hydroxyacetic acid-N-isopropyl-anilide and 50 ml of acetone, while stirring, and the mixture is stirred for 15 hours, while cooling with an ice/sodium chloride mixture. The reaction mixture is then acidified with acetic acid and concentrated under a water pump vacuum. The residue is shaken with chloroform/water and the organic phase is separated off, dried with sodium sulphate and filtered. The solvent is carefully distilled off from the filtrate under a water pump vacuum. 9.3 g (94% of theory) of 5-(1-methyl-2-chloro-2,3,3-trifluoro-1-cyclobutyl)-1,3,4-thiadiazol -2-yl-oxyacetic acid-N-isopropyl-anilide are obtained as an oily residue of refractive index $n_D^{20}=1.5169$.

The compounds of the formula (I) or (Ia) listed in the following Table 1, for example, can also be prepared analogously to Example 1 and in accordance with the general description of the preparation process according to the invention.

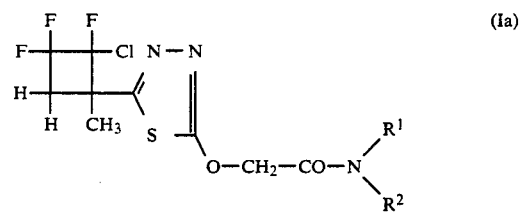

TABLE 1

| Example No. | R$^1$ | R$^2$ | Physical Data |
|---|---|---|---|
| 2 | —CH$_3$ | —CHC$_2$H$_5$<br>\|<br>CH$_3$ | $n_D^{20}$ = 1.4839 |
| 3 | —CH$_3$ | ⟨phenyl⟩ | $n_D^{20}$ = 1.5285 |
| 4 | —C$_2$H$_5$ | ⟨phenyl⟩ | |

TABLE 1-continued

Examples of the compounds of the formula (Ia)

| Example No. | R¹ | R² | Physical Data |
|---|---|---|---|
| 5 | —CH(CH₃)₂ | (4-F-phenyl) | |
| 6 | —CH(CH₃)₂ | —OCH₂CH₂OC₂H₅ | |
| 7 | —CH₂—CH=CH₂ | —CH₂—CH=CH₂ | |
| 8 | —CH(CH₃)₂ | (4-CH₃-phenyl) | |
| 9 | —CH(CH₃)₂ | (4-OCH₃-phenyl) | |
| 10 | —CH(CH₃)₂ | (3-OCH₃-phenyl) | |
| 11 | —CH(CH₃)₂ | (4-Cl-phenyl) | |
| 12 | —C₂H₅ | (3,4-di-CH₃-phenyl) | |
| 13 | —CH₃ | (4-F-phenyl) | |
| 14 | —CH₃ | cyclohexyl | |
| 15 | —(CH₂)₆— | | |
| 16 | —CH—(CH₂)₄—<br>\|<br>CH₃ | | |

STARTING SUBSTANCES OF THE FORMULA (II) AND (IV)

Example (II-1)/(IV-1)

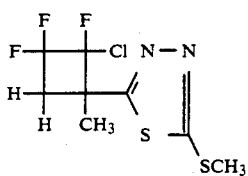
(IV-1)

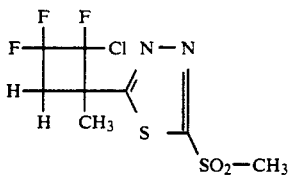
(II-1)

22.1 g (0.10 mol) of 1-methyl-2-chloro-2,3,3-trifluorocyclobutane-1-carbonylchloride are added dropwise to a mixture, cooled to −5° C., of 12.2 g (0.10 mol) of methyl dithiocarbazate, 9.0 g (0.11 mol) of pyridine and 100 mol of tetrahydrofuran, and after the cooling bath has been removed the mixture is stirred for 2 hours. 50 ml of concentrated sulphuric acid are then added, while cooling with ice, and the reaction mixture is stirred at 20° C. for 15 hours. It is then diluted with ice-water and shaken with chloroform The organic phase is separated off, washed with water, dried with sodium sulphate and filtered. The solvent is carefully distilled off from the filtrate under a water pump vacuum.

29 g (about 100% of theory) of 2-methylthio-5-(1-methyl2-chloro-2,3,3-trifluoro-1-cyclobutyl)-1,3,4-thiadiazole are obtained as an oily residue. This product (29 g) is taken up in 80 ml of acetic acid, and after addition of 0.5 g of sodium tungstate, 25 ml of a 30% strength aqueous hydrogen peroxide solution are added dropwise. The reaction mixture is stirred at 40° C. to 50° C. for 60 minutes and then diluted with ice-water. The oily product which separates out during this operation is taken up in chloroform and this solution is washed with water and 5% strength sodium bicarbonate solution, dried with sodium sulphate and filtered The solvent is distilled off from the filtrate under a water pump vacuum and the solid residue is recrystallized from isopropanol.

13.1 g (41% of theory) of 2-methylsulphonyl-5-(1-methyl2-chloro-2,3,3-trifluoro-1-cyclobutyl)-1,3,4-thiadiazole of melting point 63° C. are obtained

STARTING COMPOUND OF THE FORMULA (Va)

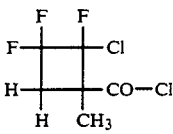

1st Stage

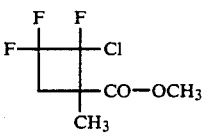

750 g (7.5 mol) of methyl methacrylate, 700 g (6.0 mol) of chlorotrifluoroethane and 3 g of hydroquinone are heated at 120° C. in a steel autoclave for 12 hours. The product is fractionated directly.

780 g (60% of theory) of methyl 1-methyl-2-chloro-2,3,3-trifluoro-cyclobutane-1-carboxylate are obtained, boiling point: 57°–59° C./18.6 mbar.

2nd Stage

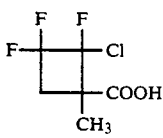

573 g(2.65 mol) of methyl 1-methyl-2-chloro-2,3,3-trifluor-cyclobutane-1-carboxylate, 233 g (5.8 mol) of sodium hydroxide and 1000 ml of water are stirred at 80° C. for three hours. The mixture is acidifed with concentrated hydrochloric acid and extracted with dichloromethane, and the organic phases are dried and distilled. 472 g (88% of theory) of 1-methyl-2-chloro2,3,3-trifluoro-cyclobutane-1-carboxylic acid are obtained, boiling point: 112°-116° C./21.4 mbar (60% transisomer, 40% cis-isomer).

3rd Stage

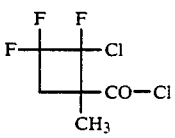

220 g (1.09 mol) of 1-methyl-2-chloro-2,3,3-trifluorocyclobutane-1-carboxylic acid are stirred with 250 g (1.23 mol) of phthaloyldichloride at room temperature overnight. The acid chloride is then distilled off.

238 g (99% of theory) of 1-methyl-2-chloro-2,3,3-trifluoro-cyclobutane-1-carbonyl chloride are obtained, boiling point: 54°-56° C./30 6 mbar

USE EXAMPLES

Example A

Test on transplated paddy rice

Solvent: 5 parts by weight of acetone
Emulsifier: 1 part by weight of benzyloxypolyglycol ether To produce a suitable preparation of active compound, 1 part by weight of active compound is mixed with the stated amount of solvent, the stated amount of emulsifier is added and the concentrate is diluted to the desired concentration.

Plant receptacles (surface area 1/5000 are) are filled with soil from a paddy-field Two rice plants (variety: Kinmaze) in the 2-3 eaf stage (about 10 cm high) are transplanted into the receptacles Seeds of Echinochloa crus galli are sown in the moist earth. 5 days after transplanting the rice, the soil is covered with water to a depth of 3 cm. The active compound preparation is applied to the surface of the water. The concentration of the active compound in the preparation is of no importance, only the amount of active compound applied per unit area being decisive.

After applying the active compound, a vertically ascending flow of water having a velocity of 2-3 cm per day is set up through the plant receptacles for 2 days. After this the test batches are kept under overflow conditions, in which the water depth is 3 cm.

After 4 weeks the degree of damage to the plants is evaluated in % damage (or weed action) in comparison to an untreated control.

The figures denote

0 % = no action (like untreated control)
100 % = total destruction

In this test, the outstanding tolerance of the active compounds according to the invention—in particular of compounds from Examples 1 and 3 —by rice is shown, at the same time as a very good action against weeds.

Example B

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test also, the compounds of the formula (I) according to the invention exhibit a very good activity.

It will be understood that the specification and examples are illustrative but not limitative of the present invention and that other embodiments within the spirit and scope of the invention will suggest themselves to those skilled in the art.

We claim:

1. A cycloalkyl-substituted thiadiazolyloxyacetamide of the formula

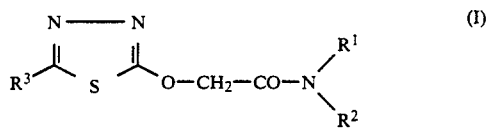

in which
R$^1$ represents C$_1$-C$_4$-alkyl, ally or proparglyl,
R$^2$ represents C$_1$-C$_6$-alkyl, C$_1$-C$_2$-alkoxy-C$_1$-C$_2$-alkyl, allyl, propargyl, cyclopentyl, cyclohexyl, cyclohexenyl, benzyl, phenyl (which is optionally substituted by fluorine, chlorine, bromine, cyano, nitro, methyl, ethyl, trifluoromethyl, methoxy or ethoxy), C$_1$-C$_6$-alkoxy or C$_1$-C$_2$-alkoxyC$_1$-C$_2$-alkoxy, or
R$^1$ and R$^2$, together with the nitrogen atom to which they bar bonded, represent piperidinyl which is optionally substituted by one to three methyl and/or ethyl radicals, or represent pyrrolidinyl which is optionally substituted by one or two methyl and/or ethyl radicals, or represent perhydroazepinyl, or represent 1,2,3,4-tetrahydroquinolinyl, and
R$^3$ represents cyclopropyl or cyclobutyl, in each case substituted by fluorine and/or chlorine and optionally additionally by methyl.

2. A compound according to claim 1 of the formula

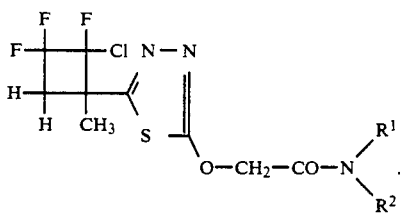

(Ia)

3. A compound according to claim 3, wherein such compound is 5-(1-methyl-2-chloro-2,3,3-trifluoro-1-cyclobutyl)1,3,4-thiadiazol-2-yl oxyacetic acid-N-isopropyl-anilide of the formula

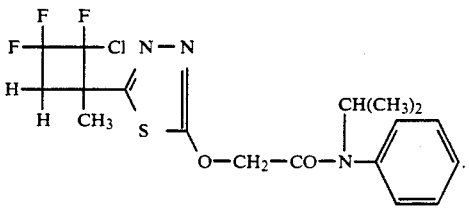

4. A compound according to claim 1, wherein such compound is 5-(1-methyl-2-chloro-2,3,3-trifluoro-1cy- clobutyl)-1,3,4-thiadiazol-2-yl oxyacetic acid-N-methylanilide of the formula

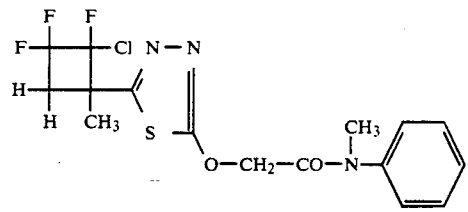

5. A herbicidal composition comprising a herbicidally effective amount of a compound according to claim 1 and a diluent.

6. A method of combatting unwanted vegetation which comprises applying to such vegetation or to a locus from which it is desired to exclude such vegetation a herbicidally effective amount of a compound according to claim 1.

7. The method according to claim 6, wherein such compound is
- 5-(1-methyl-2-chloro-2,3,3-trifluoro-1-cyclobutyl)- 1,3,4-thiadiazol-2-yl oxyacetic acid-N-isopropyl-anilide or
- 5-(1-methyl-2-chloro-2,3,3-trifluoro-1-cyclobutyl)-b 1,3,4-thiadiazol-2-yl oxyacetic acid-N-methyl-anilide.

* * * * *

UNITED STATES PATENT AND TRADEMARK OFFICE
CERTIFICATE OF CORRECTION

PATENT NO. : 5,169,427

DATED : December 8, 1992

INVENTOR(S) : Forster, et al.

It is certified that error appears in the above-identified patent and that said Letters Patent is hereby corrected as shown below:

Col. 13, line 13    Delete " claim 3 " and substitute -- claim 1 --

Col. 14, line 26    Delete " b "

Signed and Sealed this

Fifth Day of April, 1994

Attest:

BRUCE LEHMAN

*Attesting Officer*     *Commissioner of Patents and Trademarks*